US012728158B2

(12) United States Patent
Kosmatopoulos et al.

(10) Patent No.: US 12,728,158 B2
(45) **Date of Patent: *Sep. 8, 2026**

(54) COMBINATION OF MARKERS FOR PREDICTING THE RESPONSE TO Vx-001

(71) Applicant: KRIPTIC PHARMACEUTICALS LIMITED, Dublin (IE)

(72) Inventors: Kostantinos (Kostas) Kosmatopoulos, Paris (FR); Jeanne Menez-Jamet, Montrouge (FR)

(73) Assignee: KRIPTIC PHARMACEUTICALS LIMITED, Dublin (IE)

( * ) Notice: Subject to any disclaimer, the term of this patent is extended or adjusted under 35 U.S.C. 154(b) by 1308 days.

This patent is subject to a terminal disclaimer.

(21) Appl. No.: 17/617,690

(22) PCT Filed: Jun. 9, 2020

(86) PCT No.: PCT/FR2020/050975

§ 371 (c)(1), (2) Date: Dec. 9, 2021

(87) PCT Pub. No.: WO2020/249895

PCT Pub. Date: Dec. 17, 2020

(65) Prior Publication Data

US 2022/0249642 A1 Aug. 11, 2022

(30) Foreign Application Priority Data

Jun. 11, 2019 (FR) ...................................... 1906208

(51) Int. Cl.

| | |
|---|---|
| ***A61K 39/00*** | (2006.01) |
| ***A61P 35/00*** | (2006.01) |
| ***G01N 33/50*** | (2006.01) |

(52) U.S. Cl.
CPC ...... *A61K 39/001157* (2018.08); *A61P 35/00* (2018.01); *G01N 33/50* (2013.01);
(Continued)

(58) Field of Classification Search
CPC ........ A61K 39/001157; A61K 2039/54; A61K 2039/572; A61K 2039/70; A61K 2039/57;
(Continued)

(56) References Cited

FOREIGN PATENT DOCUMENTS

WO WO-2006120038 A2 * 11/2006 ............. A61K 38/08

OTHER PUBLICATIONS

Kailashiya C. et al. Telomerase based anticancer immunotherapy and vaccines approaches. Vaccine. 2017 (Year: 2017).*
(Continued)

*Primary Examiner* — Robert B Mondesi
(74) *Attorney, Agent, or Firm* — Arrigo, Lee, Guttman & Mouta-Bellum LLP

(57) ABSTRACT

The invention relates to the use of an anti-tumour vaccine composed of two peptides of nine amino acids—native cryptic TERT572 (RLFFYRKSV, SEQ ID No. 1), expressed by tumour cells, and the optimised variant thereof TERT572Y (YLFFYRKSV, SEQ ID No. 2), for the treatment of a tumour expressing telomerase reverse transcriptase (TERT), in an HLA-A*0201 patient with a normal gamma glutamine transferase (gGT) level and/or a normal lactate dehydrogenase (LDH) level.

10 Claims, 9 Drawing Sheets

Figure 1:
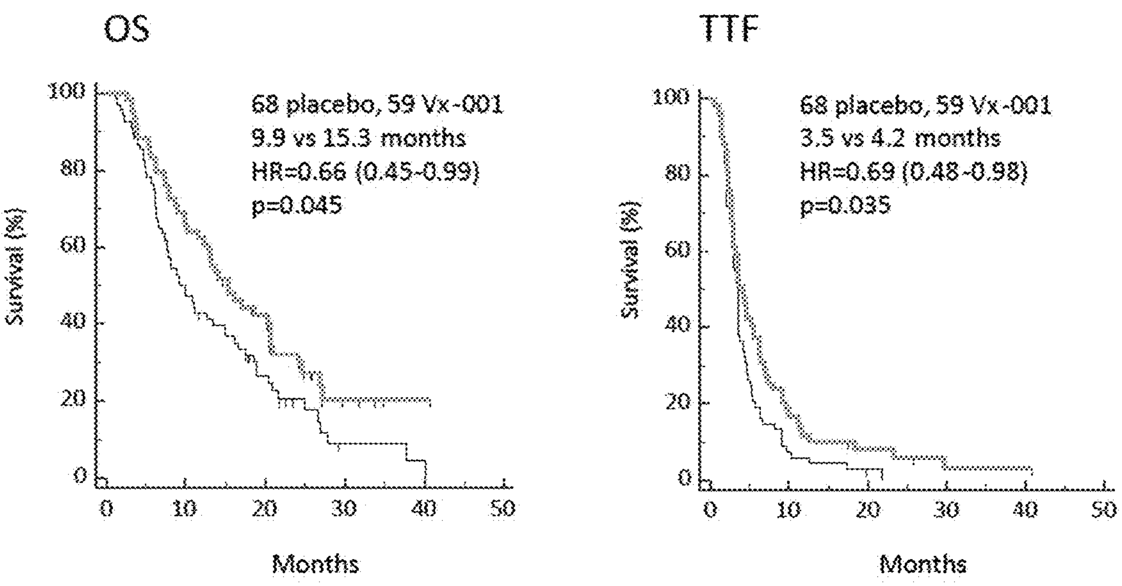

Specification includes a Sequence Listing.

(52) U.S. Cl.
CPC .... *A61K 2039/54* (2013.01); *A61K 2039/572* (2013.01); *A61K 2039/70* (2013.01); *G01N 2333/904* (2013.01); *G01N 2333/9108* (2013.01); *G01N 2333/91085* (2013.01); *G01N 2800/52* (2013.01)

(58) Field of Classification Search
CPC ........ A61K 2039/812; A61K 2039/852; A61K 38/08; A61K 2039/86; A61P 35/00; G01N 33/50; G01N 2333/904; G01N 2333/9108; G01N 2333/91085; G01N 2800/52
See application file for complete search history.

(56) References Cited

OTHER PUBLICATIONS

Aykan NF. et al. Objective response rate assessment in oncology: Current situation and future expectations. World J Clin Oncol. 2020 (Year: 2020).*

Bozkaya, Y. et al. Prognostic significance of gamma-glutamyl transferase in patients with metastatic non-small cell lung cancer. Expert Review of Molecular Diagnostics. 2019 (Year: 2019).*

Georgoulias, V. et al. A Multicenter Randomized Phase IIb Efficacy Study of Vx-001, a Peptide-Based Cancer Vaccine as Maintenance Treatment in Advanced Non-Small-Cell Lung Cancer: Treatment Rationale and Protocol Dynamics. Clin Lung Cancer (2013) (Year: 2013).*

Kotsakis A. et al. A phase II trial evaluating the clinical and immunologic response of HLA-A2(+) non-small cell lung cancer patients vaccinated with an hTERT cryptic peptide. Lung Cancer. 2014 (Year: 2014).*

Lin, G. et al. Prognostic significance of PD-L1 expression and tumor infiltrating lymphocyte in surgically resectable non-small cell lung cancer. Oncotarget. 2017 (Year: 2017).*

Kotsakis et al., "Clinical outcome of patients with various advanced cancer types vaccinated with an optimized cryptic human telomerase reverse transcriptase (TERT) peptide: results of an expanded phase II study," Annals of Oncology, 23: 442-449 (2012).

Georgoulias et al., "A Multicenter Randomized Phase IIb Efficacy Study of Vx-001, a Peptide-Based Cancer Vaccine as Maintenance Treatment in Advanced Non-Small-Cell Lung Cancer: Treatment Rationale and Protocol Dynamics," Clinical Lung Cancer, 14 (4): 461-465 (2013).

Gridelli et al., "Clinical activity of a htert (vx-001) cancer vaccine as post-chemotherapy maintenance immunotherapy in patients with stage IV non-small cell lung cancer: final results of a randomised phase 2 clinical trial," British Journal of Cancer (2020).

Menez-Jamet et al., "Optimized tumor cryptic peptides: the basis for universal neo-antigen-like tumor vaccines," Annals of Translational Medicine, 4 (14): 266 (2016).

Ferrucci et al., "Baseline neutrophils and derived neutrophil-to-lymphocyte ratio: prognostic relevance in metastatic melanoma patients receiving ipilimumab," Annals of Oncology, 27: 732-738 (2016).

Mezquita et al., "Association of Lung Immune Prognostic Index with Immune Checkpoint Inhibitor Outcomes in Patients with Advanced Non-Small Cell Lung Cancer," JAMA Oncology, 4 (3): 351-357 (2018).

Tourdot et al., "A general strategy to enhance immunogenicity of low-affinity HLA-A2.1-associated peptides: implication in the identification of cryptic tumor epitopes," European Journal of Immunology, 30 (12): 3411-3421 (2000).

"Vaxon-biotech>VX-001" <<https://web.archive.org/web/20170408155422/http://vaxon-biotech.com/>page_id=122>> (2017) (retrieved Mar. 27, 2020).

"Novel Vaccine Shows Association with Survival Based on Smoking History in Patients with Advanced NSCLC," <<https://www.targetedonc.com/conference/esmo-2017/novel-vaccine-shows-association-with-survival-based-on-smoking-history-in-patients-with-advanced-nsclc>> 2017) (retrieved Mar. 27, 2020).

"Lung cancer: Vaxon announces results of its Vx-001 therapeutic vaccine Phase IIb trial -Andrew Lloyd & Associates," <<https://ala.com/vaxon-announces-results-of-its-phase-iib-lung-cancer-trial-of-vx-001-a-therapeutic-vaccine-based-on-optimized-cryptic-peptides>> (2017) (retrieved Mar. 27, 2020).

International Search Report issued in corresponding International Patent Application No. PCT/FR2020/050975 dated Sep. 17, 2020.

* cited by examiner

COMBINATION OF MARKERS FOR PREDICTING THE RESPONSE TO Vx-001

SEQUENCE LISTING SUBMISSION VIA EFS-WEB

A computer readable text file, entitled "SequenceListing.txt" created on Dec. 8, 2021 with a file size of 602 bytes contains the sequence listing for this application and is hereby incorporated by reference in its entirety.

FIELD OF THE INVENTION

The present invention concerns the field of anti-cancer immunotherapy, and more particularly the field of anti-tumor vaccination.

TECHNOLOGICAL BACKGROUND

The general state of patients suffering from cancer is assessed by routine blood-tests, including the level of LDH Glutamine (lactate dehydrogenase), gGT (gamma Glutamine Transferase), ALP (Alkaline Phosphatase), markers of liver function and inflammation, and/or a blood count enabling determination of the absolute number and ratio between neutrophils and lymphocytes as well as the platelet count.

These constants are known to be prognostic markers in patients suffering from cancer, the patients with a deteriorated general state having a poorer life prognosis. It has also been shown that this could influence the response to certain treatments, in particular Immune Checkpoint Inhibitors, which are substances developed in recent years that have revolutionized the management of certain cancers (Ferrucci et al., Annals Oncol. 2016).

Anti-cancer immunotherapy is provided to stimulate the recognition by cytotoxic T lymphocytes (CTLs) of peptides derived from tumor antigens that are presented on the surface of the tumor cell by Class I human leukocyte antigens (HLA-I). The peptides targeted by the CTLs may be dominant or cryptic according to their affinity for the HLA molecules Tumor-associated antigens (TAAs) are frequently expressed both by tumor cells and normal tissues, contrary to neoantigens, which are tumor-specific and most often patient-specific. TAAs have the advantage of being expressed by a great many tumors contrary to neoantigens, but have the drawback of being subject to tolerance mechanisms that prevent auto-immunity, i.e. the recognition of self antigens by an individual's immune system.

Telomerase reverse transcriptase (TERT), an enzyme involved in tumor cell immortalization, is an antigen of TAA type expressed by numerous tumors (85% of tumors). To get around the problem of tolerance by the immune system in relation to TAAs, while targeting an antigen widely expressed by tumors, the inventors have provided a vaccine (Vx-001) targeting a cryptic peptide of TERT, that is to say a TERT peptide that has a low affinity for the HLA-A*0201 molecule (which is the CMH-I molecule most often expressed in humans) and forms unstable peptide/HLA-I complexes (Tourdot S. et al., 2000, Menez-Jamet J. et al., 2016). Given the strong correlation between the affinity for HLA-I and immunogenicity, this cryptic peptide is naturally not immunogenic. To be used as a vaccine against cancer, this cryptic peptide has been optimized to strengthen its immunogenicity.

Vx-001 is thus an anti-tumor therapeutic vaccine composed of two peptides of nine amino acids; the native cryptic peptide TERT572 (RLFFYRKSV, SEQ ID No. 1), expressed by tumor cells, and its optimized variant TERT572Y (YLFFYRKSV, SEQ ID No. 2). These two peptides are administered separately, each with the adjuvant Montanide ISA51®VG (a mixture of a highly purified mineral oil (Drakeol 6VR) and a surfactant (Mannide monooleate)). TERT572Y, an immunogenic optimized peptide, is used for the first two vaccinations, to trigger a strong immune response. The native peptide TERT572 is administered in the following vaccination steps, in order to select, from among all the T lymphocytes stimulated by TERT572Y, those which have the highest specificity for native TERT572, which is present on the surface of the tumor cells associated with HLA-A*0201.

Vx-001 has recently been tested in patients with metastatic or recurrent stage I-III NSCLC (non-small cell lung cancer) in a randomized phase IIb clinical trial (Vx-001-201). The vaccine protocol in this trial comprised 6 vaccinations at 3-week intervals (2 vaccinations with TERT572Y, then 4 vaccinations with TERT572), followed by boosters every 12 weeks (with TERT572) until the disease progressed (Georgoulias et al., Clin Lung Cancer. 2013).

The patients included expressed HLA-A*0201 and had a tumor expressing TERT. The main objective of the study was to track overall survival. The results of this study were not statistically significant overall. However, Vx-001 showed significant effectiveness in certain patients. The inventors have thus studied whether certain blood constants could be linked to a clinical response or lack of response to the vaccine. This study led to a stratification of patients, with identification of categories of patients for whom vaccination with Vx-001 proved statistically beneficial.

SUMMARY OF THE INVENTION

The inventors have shown that the anti-tumor vaccine Vx-001 provides a statistically significant benefit to patients having a normal level of gGT and/or a normal level of LDH, the patients having normal levels of gGT and LDH responding particularly well to the treatment. Finer stratification showed that male patients having a non-squamous tumor responded particularly well to the treatment.

The present invention thus relates to the use of Vx-001 in a method of treating a tumor expressing telomerase reverse transcriptase (TERT), in an HLA-A*0201 patient having a normal level of gamma Glutamine Transferase (gGT) and/or a normal level of lactate dehydrogenase (LDH), preferably in a male patient having a non-squamous tumor.

The present invention also relates to a method for determining in vitro whether an HLA-A*0201 patient suffering from a TERT-expressing tumor is likely to favorably respond to an anti-cancer vaccination with Vx-001, comprising measuring the levels of gGT and LDH of the patient, who is likely to respond favorably to Vx-001 if at least one of these levels is normal.

LIST OF THE DRAWINGS

FIG. 1: OS and TTF in patients having a normal LDH serum level. Thick gray curve: patients having received Vx-001; black curve in thin line: patients having received a placebo.

Figure 2:
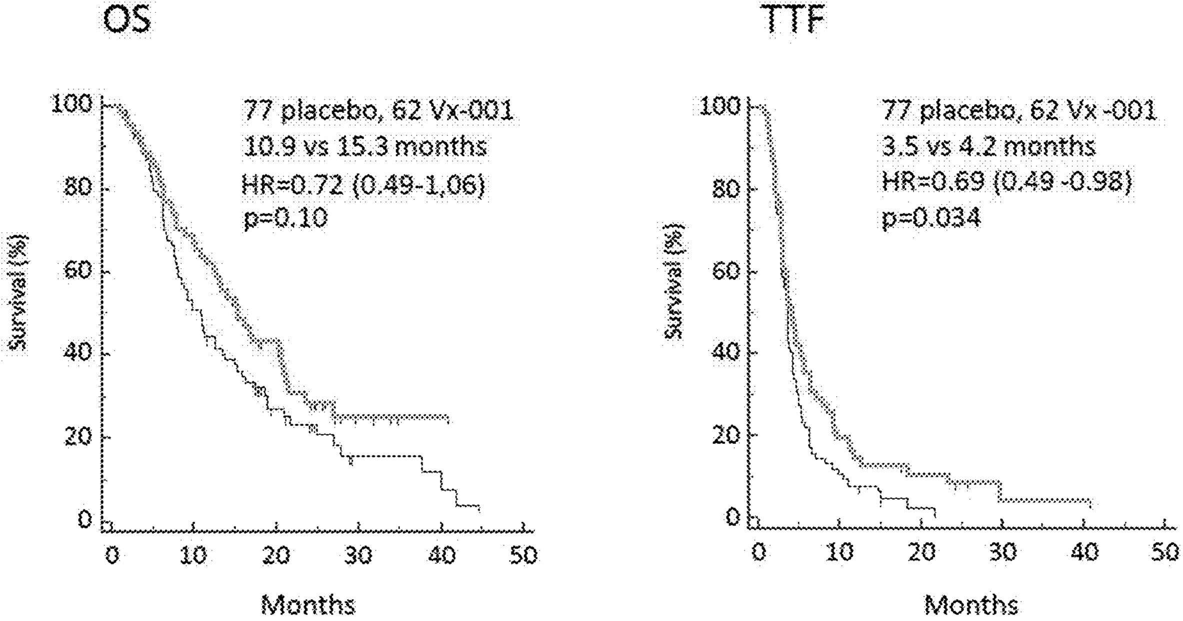

FIG. 2: OS and TTF in patients having a normal gGT serum level. Thick gray curve: patients having received Vx-001; black curve in thin line: patients having received a placebo.

Figure 3:
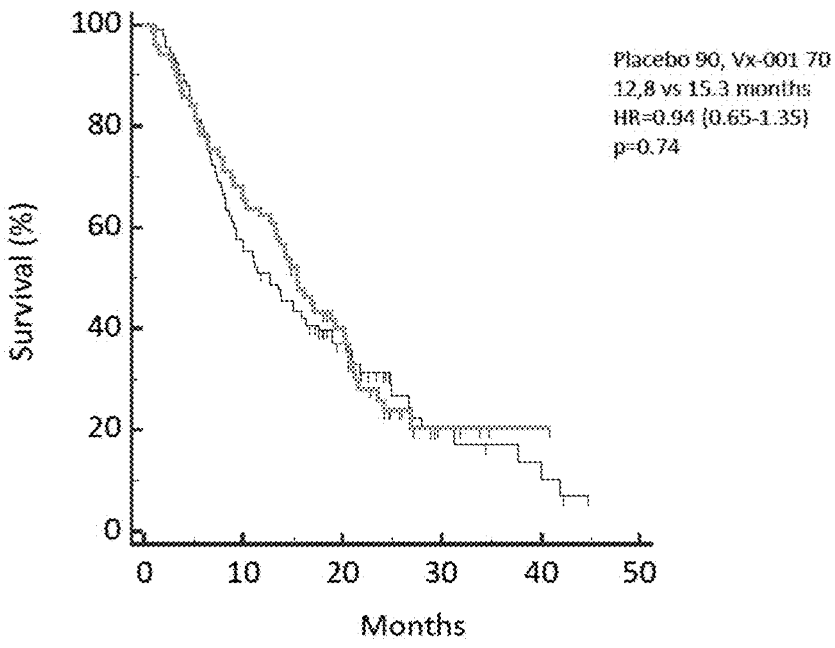

FIG. 3: Clinical response in patients having a normal ALP serum level. Thick gray curve: patients having received Vx-001; black curve in thin line: patients having received a placebo.

Figure 4:
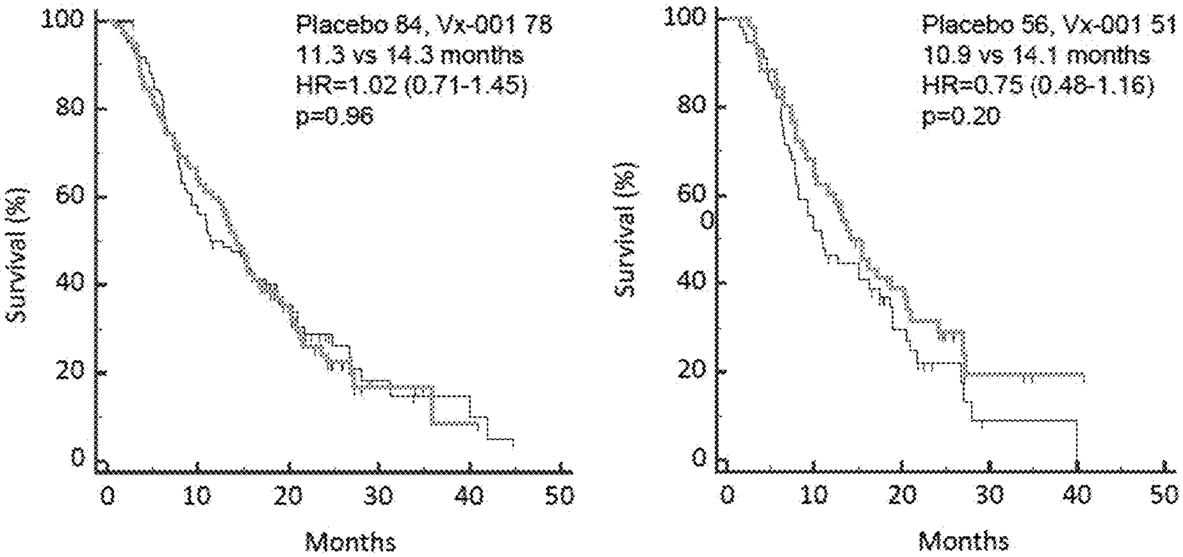

FIG. 4: Clinical response to Vx-001 and absolute number of neutrophils. Thick gray curve: patients having received Vx-001; black curve in thin line: patients having received a placebo.

Figure 5:
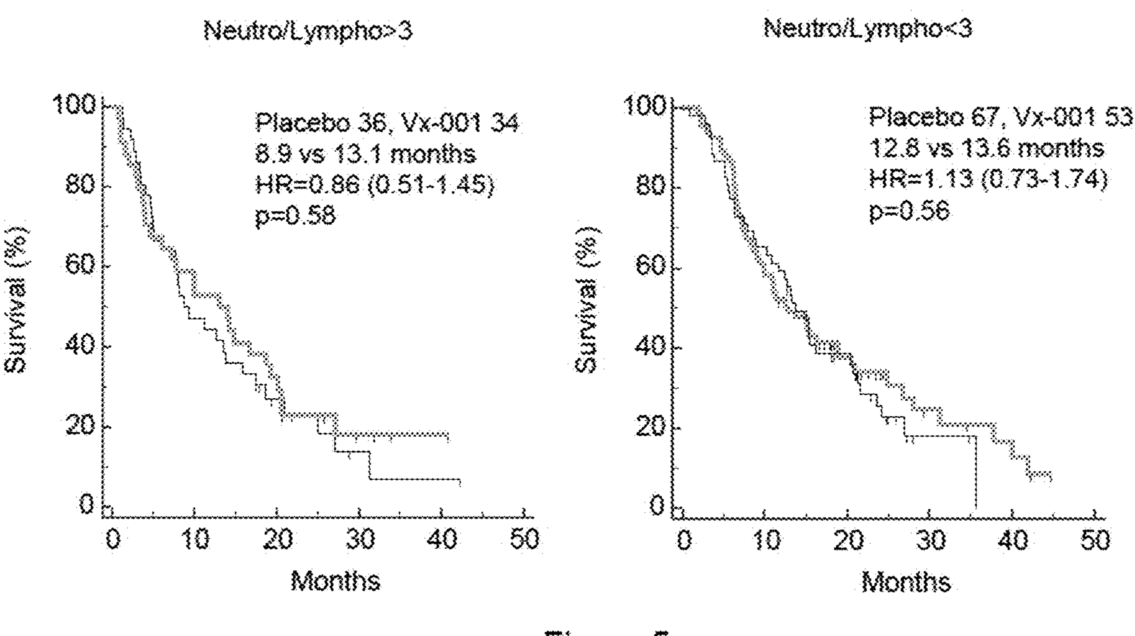

FIG. 5: Clinical response to Vx-001 and ratio between neutrophils and lymphocytes. Thick gray curve: patients having received Vx-001; black curve in thin line: patients having received a placebo.

Figure 6:
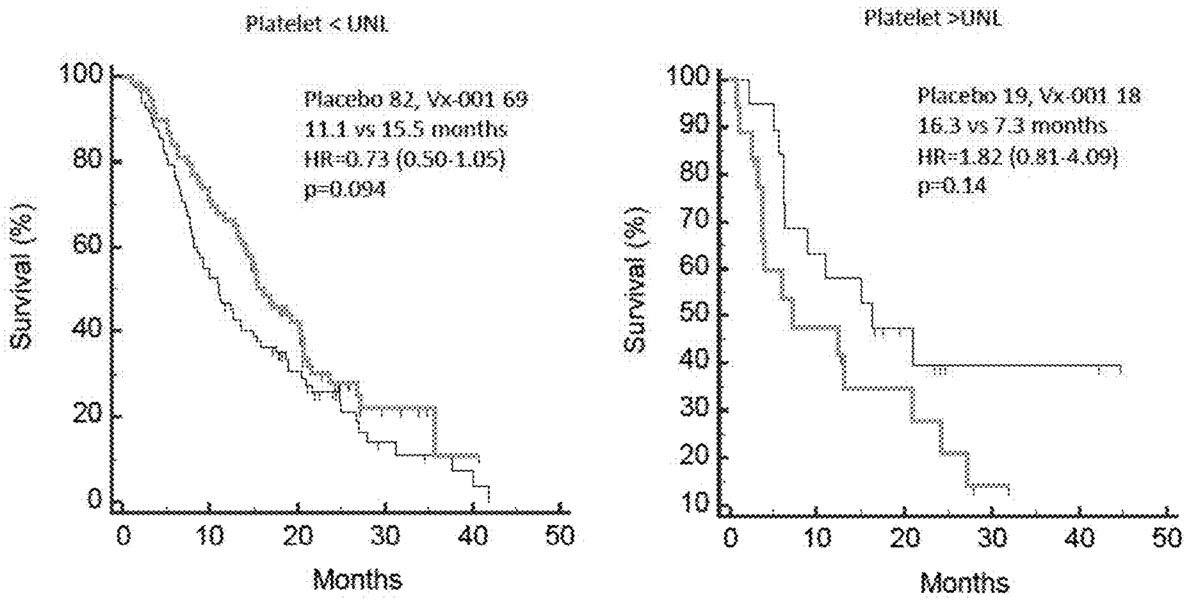

FIG. 6: Clinical response to Vx-001 and number of platelets. Thick gray curve: patients having received Vx-001; black curve in thin line: patients having received a placebo.

Figure 7:
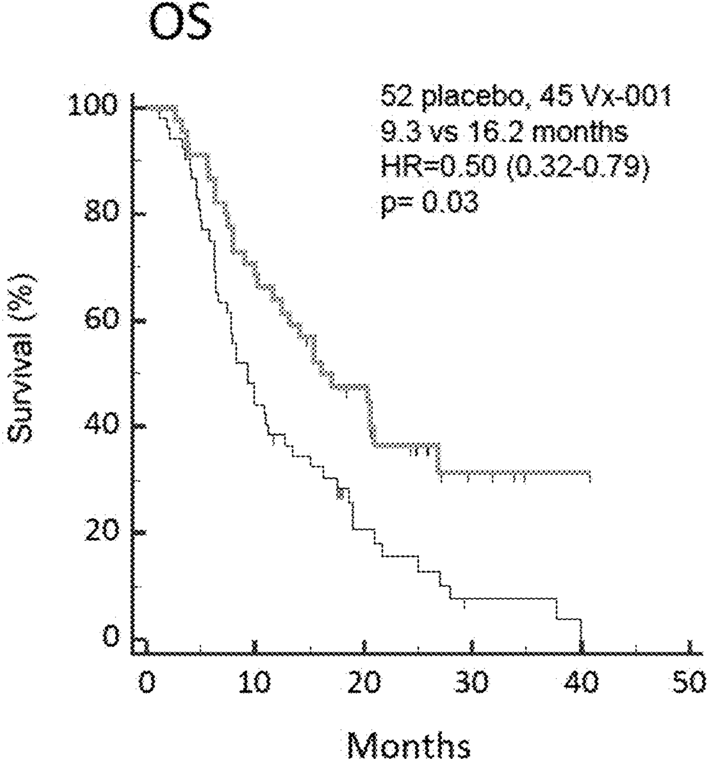
Figure 7:
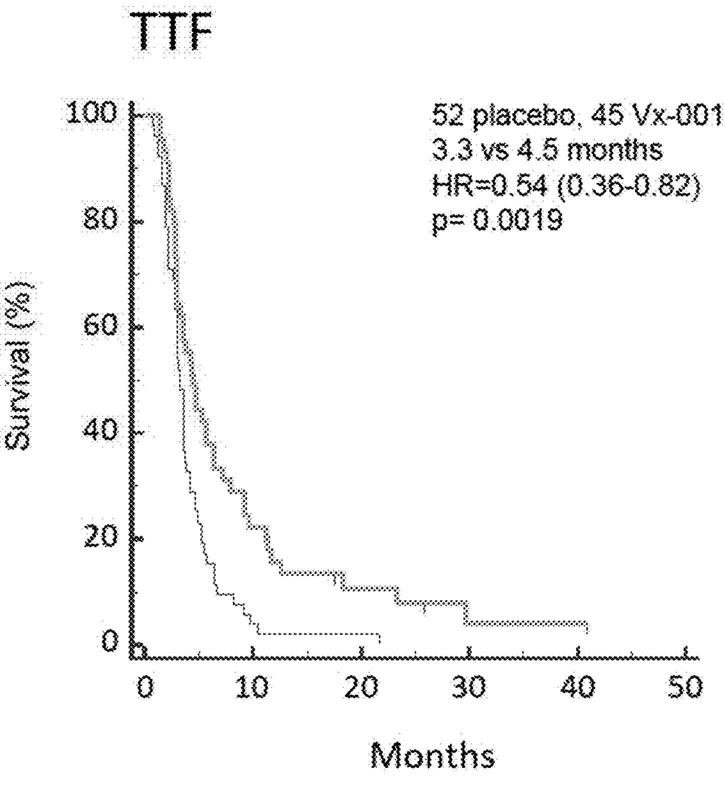

FIG. 7: OS and TTF in patients having normal LDH and gGT serum levels. Thick gray curve: patients having received Vx-001; black curve in thin line: patients having received a placebo.

Figure 8:
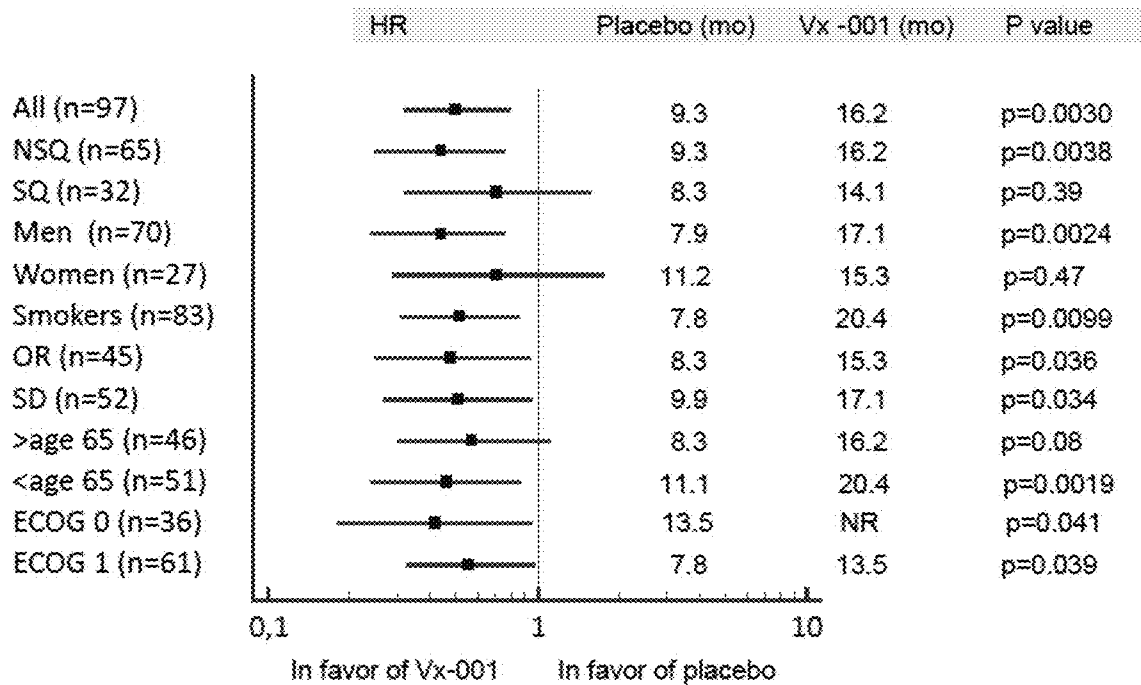

FIG. 8: Analysis of the survival of the sub-groups of patients having normal LDH and gGT serum levels. NSQ: non-squamous tumor. SQ: squamous tumor. OR: objective response to chemotherapy. SD: stable disease. ECOG: "Eastern Cooperative Oncology Group" functional index.

Figure 9:
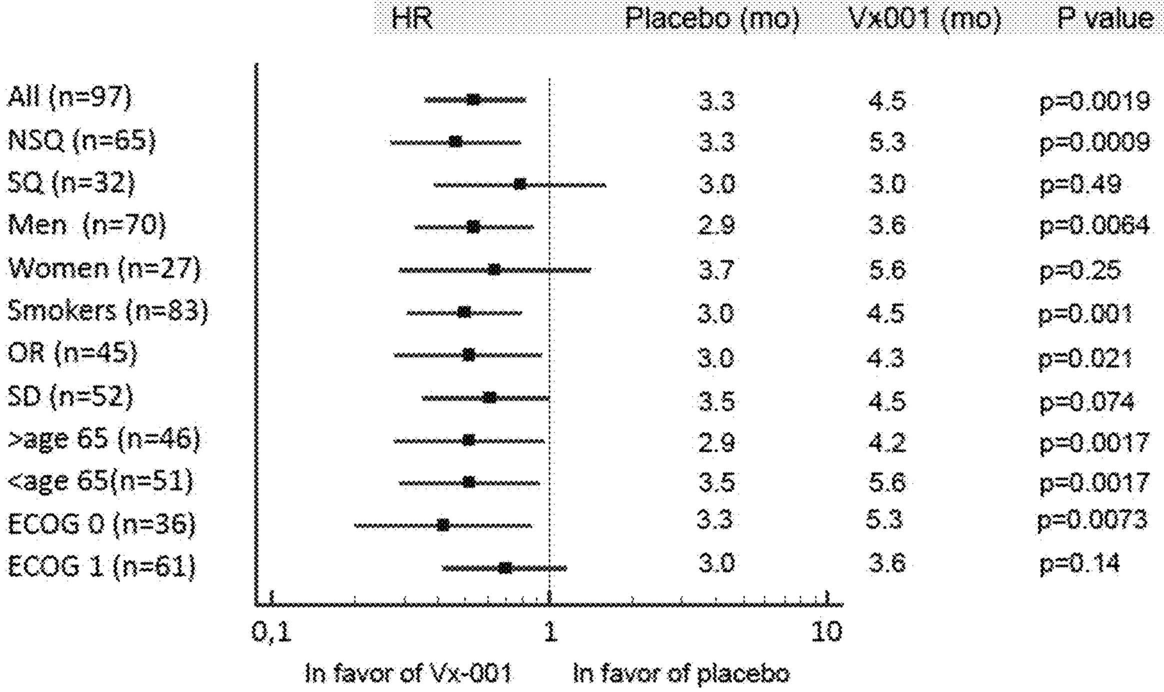

FIG. 9: Analysis of the TTF (Time to Treatment Failure), of patients having normal LDH and gGT serum levels. NSQ: non-squamous tumor. SQ: squamous tumor. OR: objective response to chemotherapy. SD: stable disease. ECOG: "Eastern Cooperative Oncology Group" functional index.

Figure 10:
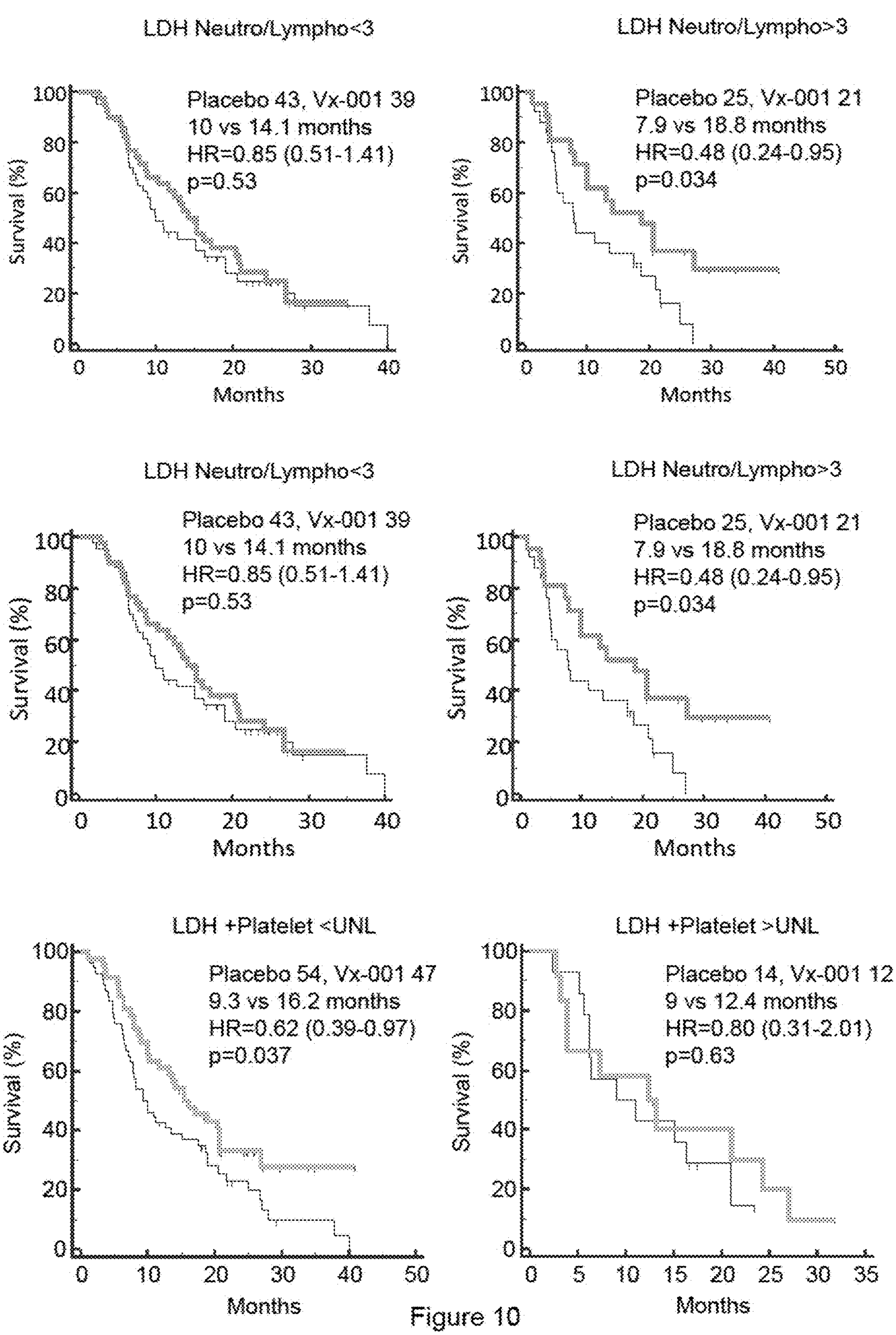

FIG. 10: Survival of patients as a function of the combination of markers studied. Thick gray curve: patients having received Vx-001; black curve in thin line: patients having received a placebo.

Figure 11:
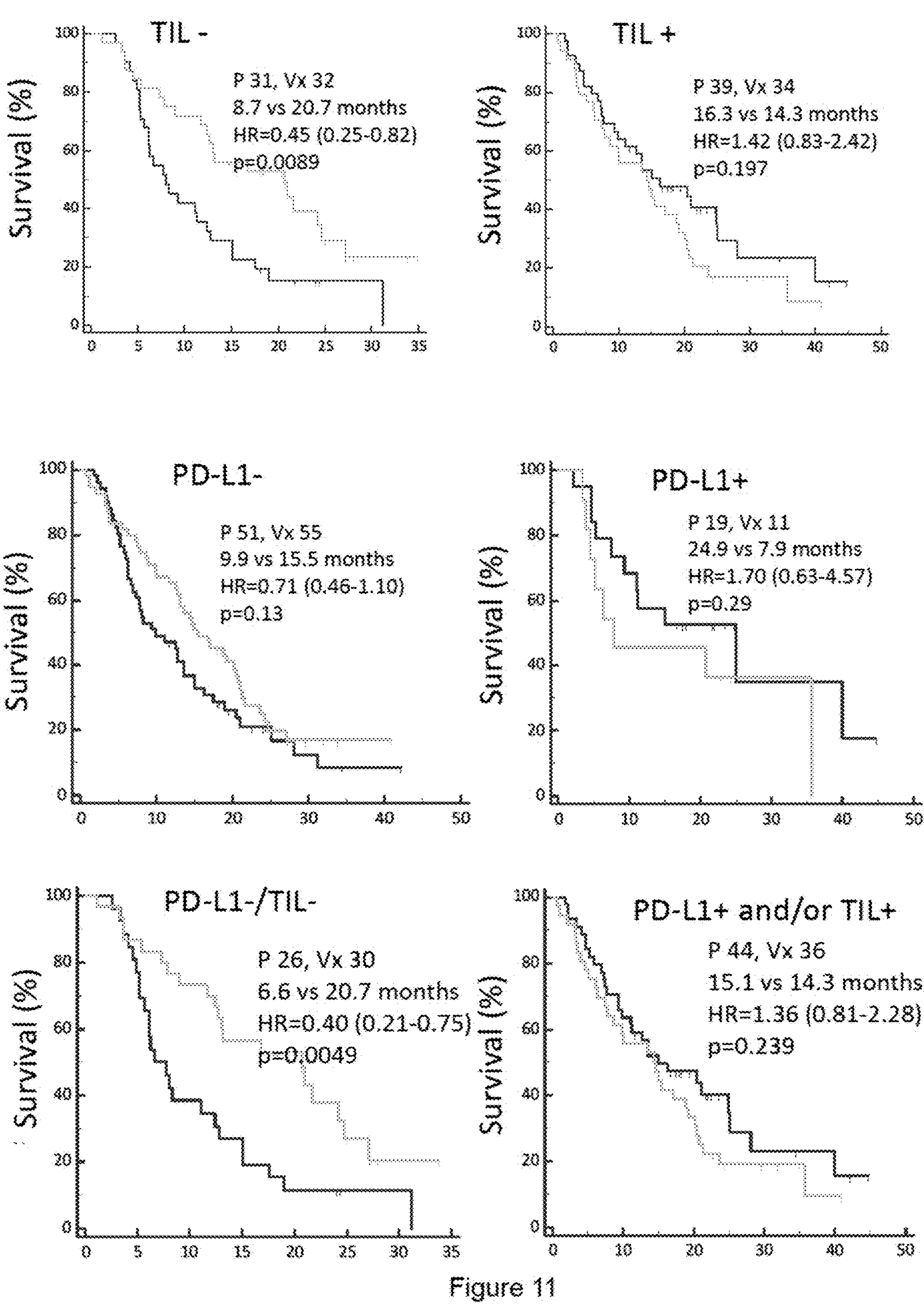

FIG. 11: Survival of patients as a function of the immunogenicity of the tumor defined by infiltration with TILs (Tumor Infiltrating Lymphocytes) and expression of PD-L1. Gray curve: patients having received Vx-001; black curve: patients having received a placebo.

Figure 12:
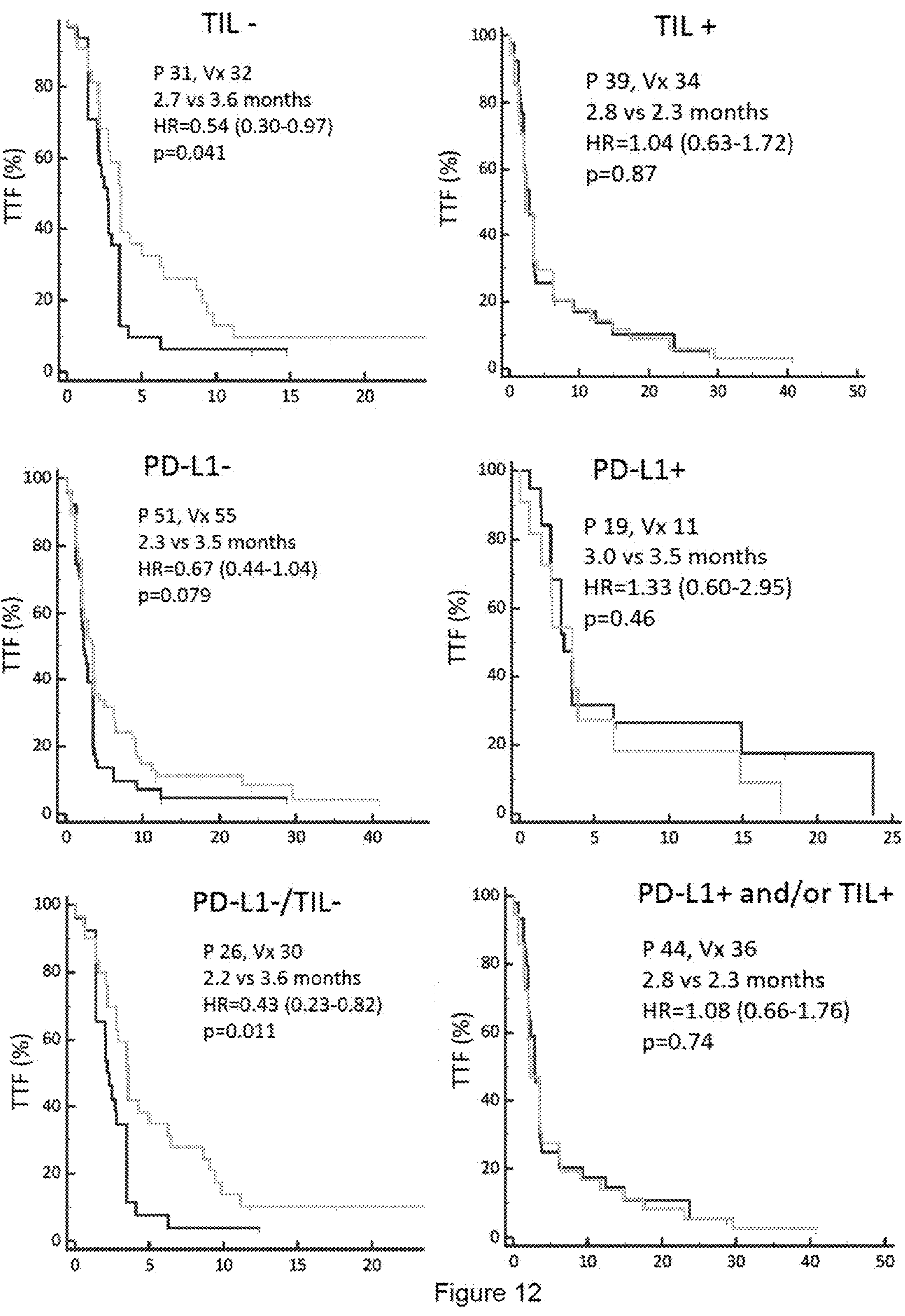

FIG. 12: TTF of patients as a function of the immunogenicity of the tumor defined by infiltration with TILs (Tumor Infiltrating Lymphocytes) and expression of PD-L1. Gray curve: patients having received Vx-001; black curve: patients having received a placebo.

Figure 13:
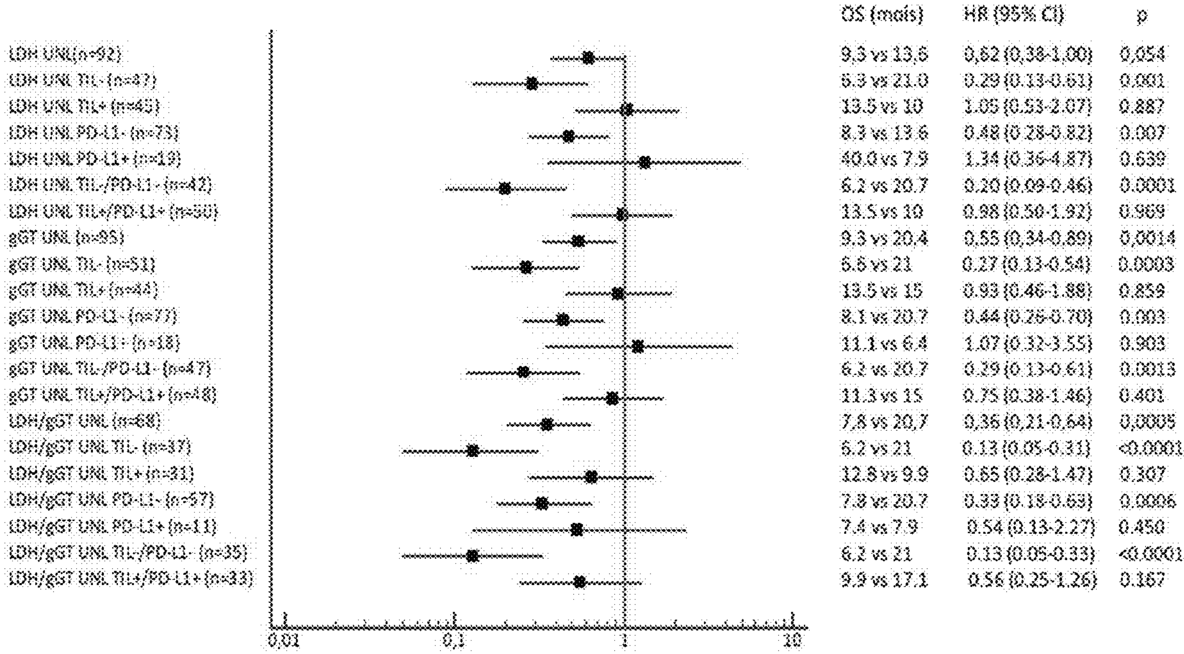
Figure 14:
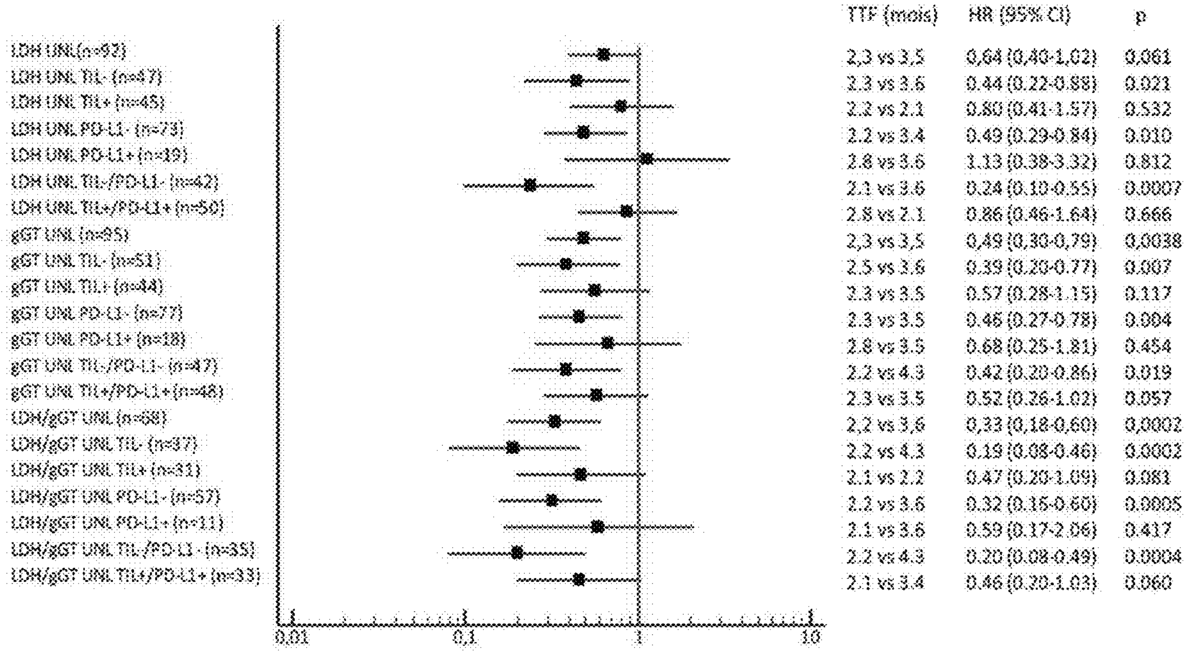

FIG. 13: Survival of patients whose tumor is non-immunogenic or immunogenic as a function of the markers studied. LDH/gGT UNL=LDH/gGT less than the upper normal limits FIG. 14: TTF of patients whose tumor is non-immunogenic or immunogenic as a function of the markers studied. LDH/gGT UNL=LDH/gGT less than the upper normal limits

DETAILED DESCRIPTION

The present invention is based on the identification of categories of patients for whom the results of the Vx-001-201 study have shown that vaccination with Vx-001 was significantly beneficial.

The present invention concerns the use of Vx-001 to treat a TERT-expressing tumor, for each of the patient categories (set forth below).

The present invention also concerns the use of the TERT572Y peptide of SEQ ID No. 2, to induce a CTL response against the cryptic epitope TERT572 of the sequence SEQ ID No. 1, for each of these patient categories.

For each of these patient categories, the invention also concerns the use of the peptide TERT572 of sequence SEQ ID No. 1 to maintain a CTL response induced by the peptide TERT572Y of SEQ ID No.2 administered to the patient in advance.

As illustrated in the experimental part below, a first category of patients consists of the HLA-A*0201 patients suffering from a TERT-expressing tumor and having a normal level of lactate dehydrogenase (LDH).

Another category of patients likely to respond favorably to vaccination by Vx-001 consists of the HLA-A*0201 patients suffering from a TERT-expressing tumor and having a normal level of gamma Glutamine Transferase (gGT).

The HLA-A*0201 patients suffering from a TERT-expressing tumor and having both a normal level of gGT and a normal level of LDH constitute a category of patients particularly likely to respond favorably to vaccination with Vx-001.

By "normal level for gGT" and "normal level of LDH" is meant levels lower than the upper normal limits (UNL) defined by each laboratory according to the technical implementation and reagents used in that laboratory. Identifying whether or not a level is normal presents no difficulty for the person skilled in the art.

The present invention thus relates to the use of Vx-001, to treat a TERT-expressing tumor, in an HLA-A*0201 patient having a normal level of gGT and/or a normal level for LDH.

By "treat" is meant here at least slowing the progression of the tumor and/or extending the survival of the patients.

According to a particular implementation of the invention, the Vx-001 is administered to a patient having a normal level of gGT and/or a normal level of LDH after having received at least one chemotherapy. Vx-001 is thus administered further to a first-line chemotherapy.

According to another particular implementation of the invention, the Vx-001 is administered to a patient suffering from a non-small cell lung cancer (NSCLC), for example a metastatic or recurrent NSCLC, said patient having a normal level of gGT and/or a normal level of LDH.

The inventors have also shown that among patients having a normal level of gGT and/or a normal level of LDH, men responded better statistically to vaccination with Vx-001 than women.

According to another particular implementation of the invention, the Vx-001 is thus administered to a male patient having a normal level of gGT and/or a normal level of LDH.

Similarly, the results of the Vx-001-201 study show that Vx-001 is statistically more effective for treating non-squamous tumors than squamous tumors.

According to another particular implementation of the invention, the Vx-001 is thus administered to a patient having a normal level of gGT and/or a normal level of LDH suffering from a non-squamous tumor.

According to another particular implementation of the invention, the Vx-001 is administered to a patient less than 65 years old having a normal level of gGT and/or a normal level of LDH.

According to another particular implementation of the invention, the Vx-001 is administered to a patient having a normal level of gGT and/or a normal level of LDH and whose cancer is no longer progressing after a chemotherapy, for example after a first-line chemotherapy.

According to another particular implementation of the invention, the Vx-001 is administered to a patient having a normal level of gGT and/or a normal level of LDH and having an ECOG score of 0.

The results of the Vx-001-201 study also show that the normal serum levels of LDH and of gGT correlate with a longer survival and a longer TTF in patients having non-immunogenic tumors. By "non-immunogenic tumor" is meant here a tumor that does not express the PD-L1 molecule, (that is to say, if at least 1% of the tumor cells express PD-L1: Tumor Proportional Score <1%) and/or which is not infiltrated by lymphocytes (that is to say, when the tumor-infiltrating lymphocytes, or TIL, are totally absent or very few in number).

According to another particular implementation of the invention, the Vx-001 is thus administered to a patient having a normal level of gGT and/or a normal level of LDH, and whose tumor does not express the PD-L1 molecule and/or is not infiltrated by lymphocytes The present invention also relates to a method for determining in vitro whether an HLA-A*0201 patient suffering from a TERT-expressing tumor is likely to respond favorably to an anti-cancer therapeutic vaccination with Vx-001, comprising a step of measuring the gGT level and the LDH level of said patient from a biological sample from said patient; according to this method, the patient is considered as likely to respond favorably to the anti-cancer vaccination if at least one of these levels is normal, this being all the more the case if the patient's levels of gGT and of LDH are both normal.

According to the method of the invention, it is considered that the probability of the patient favorably responding to the anti-cancer vaccination with Vx-001 is even higher if the tumor is non-immunogenic, that is to say if it does not express the PD-L1 molecule and/or is not infiltrated with lymphocytes.

According to the method of the invention, it is considered that the probability of the patient responding favorably to the anti-cancer therapeutic vaccination with Vx-001 is still higher if the patient furthermore presents one or more of the following characteristics:

(i) he is of the male sex (ii) he has a non-squamous tumor (iii) he is less than 65 years old (iv) he has a tumor which is no longer progressing after a first-line chemotherapy (v) he has ECOG=0.

Of course, the different modes of implemented of the invention are not exclusive of each other, and the categories of patients having several of the criteria set forth above are all the more likely to be good responders to the vaccination with Vx-001.

The present invention is further illustrated in the experimental part below, which does not limit the scope thereof.

Examples

The blood tests were carried out during the process of recruiting the patients in the clinical trial, after the chemotherapy treatment. As each laboratory applies its own tests and its own normality limits (UNLs or "Upper Normal Limits"), the data were collected from the medical file of the patients and classified according to the results obtained relative to the normality limit applied by the laboratory (Table 1). The information studied are the levels of LDH, of gGT, of ALP, the absolute number of neutrophils, the absolute number of platelets as well as the ratio between the neutrophils and the lymphocytes.

The effectiveness of the product under investigation (Vx-001) in this clinical trial was evaluated by comparing two criteria between the patients who received the product under investigation and those who received the placebo.

the "overall survival" of the patient (denoted OS)

the period during which the disease no longer progresses and the patient receives no treatment other than the product under investigation (or the placebo), called "Time to Treatment Failure", denoted TTF.

TABLE 1

Measurement of the serum levels of Lactate dehydrogenase (LDH), gamma Glutamine Transferase (gGT), Alkaline Phosphatase (ALP), the absolute number of neutrophils (ANC), the ratio of the neutrophils/lymphocytes (N/L) and of platelets (Plat).

| Patient | LDH (UNL) | gGT (UNL) | ANC >6000 | N/L >3 | Plat. (UNL) | ALP > UNL |
|---|---|---|---|---|---|---|
| 01-02-004 | L | L | N | Y | N | N |
| 01-03-007 | L | L | N | N | N | N |
| 01-03-012 | L | H | N | N | N | N |
| 01-03-018 | L | L | N | N | N | N |
| 01-03-023 | L | H | N | N | Y | N |
| 01-04-011 | L | H | N | Y | Y | Y |
| 01-05-001 | L | L | N | N | N | N |
| 01-05-011 | L | ND | N | N | N | N |
| 01-06-006 | L | L | N | N | N | N |
| 01-07-001 | H | H | N | Y | Y | Y |
| 01-08-002 | L | L | N | Y | N | N |
| 01-08-003 | L | H | Y | Y | N | N |
| 01-08-005 | L | L | N | N | N | N |
| 01-09-002 | L | L | N | N | N | N |
| 01-09-006 | H | L | N | N | N | N |
| 01-10-002 | L | L | N | N | N | N |
| 01-10-004 | H | L | N | Y | N | N |
| 02-03-001 | ND | L | N | N | Y | N |
| 02-05-002 | ND | L | N | N | N | N |
| 02-06-002 | L | L | N | N | N | N |
| 02-06-005 | H | H | N | N | N | N |
| 02-07-004 | ND | L | N | N | N | N |
| 02-07-006 | L | L | N | Y | N | N |
| 02-07-007 | ND | L | N | N | Y | ND |
| 03-01-005 | H | L | N | N | N | N |
| 03-01-008 | H | H | N | N | N | N |
| 03-02-001 | L | H | Y | Y | N | N |
| 03-02-033 | L | H | N | Y | N | Y |
| 03-02-042 | L | L | N | N | Y | N |
| 03-02-044 | L | L | N | Y | N | N |
| 03-02-056 | L | L | N | N | Y | N |
| 03-02-060 | ND | L | N | Y | N | N |
| 03-02-070 | L | L | N | N | N | N |
| 03-02-100 | L | L | Y | Y | N | N |
| 03-03-001 | L | L | N | N | Y | N |
| 03-03-012 | L | H | N | N | N | N |
| 03-03-015 | L | L | N | N | Y | ND |
| 03-03-019 | L | H | Y | Y | N | N |
| 03-03-020 | L | L | N | N | N | ND |
| 03-03-023 | L | H | N | Y | Y | ND |
| 03-03-025 | L | L | N | N | N | ND |
| 03-03-028 | H | H | N | N | N | ND |
| 03-03-031 | L | L | N | N | N | N |
| 03-03-035 | L | L | Y | N | N | N |
| 03-03-049 | L | L | N | N | N | ND |
| 03-03-058 | L | L | Y | N | N | N |
| 03-03-062 | L | L | N | N | Y | N |
| 03-03-065 | L | H | Y | Y | N | N |
| 03-03-086 | L | L | N | Y | Y | Y |
| 03-04-001 | H | L | N | Y | N | Y |
| 03-04-014 | L | L | N | N | Y | Y |
| 03-04-025 | H | L | Y | Y | N | N |
| 03-04-040 | L | L | N | N | N | N |
| 03-04-042 | L | L | Y | N | N | N |
| 03-05-006 | H | L | N | N | N | Y |
| 03-05-007 | ND | H | N | N | N | N |
| 03-06-005 | L | L | N | N | N | N |
| 03-06-009 | L | L | N | N | N | N |
| 03-06-011 | H | H | N | N | N | N |
| 03-06-012 | L | L | N | N | N | N |
| 03-06-016 | L | L | N | N | Y | N |
| 03-07-001 | ND | H | N | N | N | ND |

TABLE 1-continued

Measurement of the serum levels of Lactate dehydrogenase (LDH), gamma Glutamine Transferase (gGT), Alkaline Phosphatase (ALP), the absolute number of neutrophils (ANC), the ratio of the neutrophils/lymphocytes (N/L) and of platelets (Plat).

| Patient | LDH (UNL) | gGT (UNL) | ANC >6000 | N/L >3 | Plat. (UNL) | ALP > UNL |
|---|---|---|---|---|---|---|
| 03-07-007 | H | L | Y | Y | Y | N |
| 03-07-008 | L | L | Y | Y | N | N |
| 03-07-013 | L | L | N | Y | N | Y |
| 03-07-021 | ND | ND | N | N | N | N |
| 03-07-028 | H | L | N | N | N | N |
| 03-07-030 | L | L | N | Y | N | N |
| 03-07-040 | H | L | Y | Y | N | N |
| 03-07-060 | L | L | N | Y | N | N |
| 03-07-066 | L | L | N | N | N | N |
| 03-07-071 | L | L | N | N | N | N |
| 03-08-013 | H | H | N | Y | N | N |
| 03-08-014 | L | L | N | N | N | N |
| 03-10-001 | L | L | N | N | N | N |
| 04-01-010 | L | L | N | N | N | N |
| 04-01-023 | L | L | N | N | N | N |
| 04-01-057 | L | H | N | N | N | Y |
| 04-02-002 | ND | ND | N | Y | N | N |
| 04-02-004 | L | L | N | N | N | N |
| 04-03-008 | L | L | Y | Y | N | N |
| 04-03-010 | H | L | N | N | N | N |
| 04-03-011 | L | L | N | N | N | N |
| 04-04-002 | L | L | N | Y | N | Y |
| 04-05-002 | L | L | N | Y | N | N |
| 04-05-006 | H | L | Y | Y | N | N |
| 04-05-026 | L | L | N | N | N | N |
| 04-05-036 | L | H | Y | N | N | N |
| 04-05-046 | ND | L | N | Y | N | N |
| 04-06-001 | L | H | N | N | N | N |
| 04-06-002 | H | L | N | N | N | N |
| 04-07-007 | H | L | N | N | N | N |
| 04-07-012 | H | L | N | N | N | N |
| 04-07-013 | L | L | N | N | N | N |
| 04-07-017 | L | L | N | Y | Y | N |
| 04-07-021 | ND | ND | N | N | N | N |
| 04-07-029 | H | L | N | N | N | N |
| 04-09-005 | L | L | Y | Y | N | N |
| 04-10-007 | ND | ND | Y | Y | N | Y |
| 04-10-008 | H | ND | N | Y | N | N |
| 04-10-014 | L | L | N | Y | N | N |
| 04-10-024 | L | L | Y | Y | N | Y |
| 04-10-025 | ND | L | N | Y | N | N |
| 04-10-031 | H | L | N | N | N | Y |
| 04-10-034 | ND | L | N | Y | N | N |
| 04-12-001 | L | L | N | N | N | N |
| 04-12-002 | ND | L | N | Y | N | N |
| 04-12-009 | L | L | N | N | N | N |
| 04-13-003 | L | L | N | N | N | N |
| 04-13-004 | L | L | N | N | N | N |
| 04-13-011 | ND | L | N | Y | N | Y |
| 04-13-015 | L | L | N | Y | N | Y |
| 05-01-013 | L | L | N | Y | N | N |
| 05-03-003 | L | L | N | N | Y | N |
| 05-04-001 | H | L | N | Y | N | N |
| 05-04-010 | L | L | N | N | N | N |
| 05-04-012 | L | H | N | Y | Y | Y |
| 05-04-014 | L | L | N | N | N | N |
| 05-06-005 | L | L | Y | Y | N | N |
| 05-07-006 | ND | ND | N | N | N | N |
| 05-07-009 | L | L | N | Y | N | N |
| 05-07-012 | L | L | N | Y | N | N |
| 05-07-015 | L | L | N | Y | N | N |
| 05-07-016 | H | L | N | N | N | N |
| 05-08-002 | H | L | N | N | Y | N |
| 05-08-027 | L | L | N | N | N | N |
| 05-09-004 | L | L | N | N | ND | Y |
| 05-09-006 | H | H | Y | N | ND | N |
| 05-09-008 | L | L | N | Y | N | N |
| 05-10-008 | H | L | N | Y | N | N |
| 05-11-001 | ND | L | N | N | N | N |
| 05-11-007 | L | L | N | N | Y | N |
| 05-13-005 | L | L | N | Y | N | N |
| 05-13-006 | L | L | Y | Y | N | N |

TABLE 1-continued

Measurement of the serum levels of Lactate dehydrogenase (LDH), gamma Glutamine Transferase (gGT), Alkaline Phosphatase (ALP), the absolute number of neutrophils (ANC), the ratio of the neutrophils/lymphocytes (N/L) and of platelets (Plat).

| Patient | LDH (UNL) | gGT (UNL) | ANC >6000 | N/L >3 | Plat. (UNL) | ALP > UNL |
|---|---|---|---|---|---|---|
| 06-01-002 | L | ND | Y | Y | Y | ND |
| 07-02-004 | L | H | N | N | N | N |
| 07-02-013 | L | ND | Y | N | Y | N |
| 07-03-002 | ND | ND | N | Y | N | N |
| 07-03-004 | L | L | Y | Y | N | N |
| 07-03-009 | H | L | N | Y | Y | Y |
| 07-03-011 | H | L | Y | N | Y | N |
| 07-03-013 | L | L | N | N | Y | Y |
| 07-03-015 | L | H | Y | Y | Y | Y |
| 07-03-016 | L | ND | N | N | N | N |
| 07-03-019 | H | L | N | N | N | Y |
| 07-03-021 | L | ND | N | Y | N | N |
| 07-03-022 | H | ND | N | N | N | N |
| 07-03-030 | L | L | N | N | N | N |
| 07-03-032 | L | L | Y | Y | N | N |
| 07-04-006 | L | ND | N | Y | N | N |
| 07-04-010 | L | L | N | N | N | N |
| 07-04-011 | L | ND | N | N | N | N |
| 07-04-020 | L | L | N | N | N | N |
| 07-04-022 | ND | L | N | N | N | N |
| 07-04-023 | L | L | N | N | N | N |
| 07-05-001 | L | L | N | N | N | N |
| 07-06-004 | L | L | N | N | N | Y |
| 07-06-006 | L | H | N | Y | N | N |
| 07-06-016 | L | L | N | N | N | N |
| 07-06-018 | H | H | N | N | N | N |
| 07-06-020 | L | H | N | N | N | Y |
| 07-06-024 | L | H | N | N | Y | Y |
| 07-07-011 | L | L | N | N | N | N |
| 07-08-001 | L | L | N | N | N | N |
| 07-09-001 | L | L | N | N | Y | N |
| 07-10-002 | L | H | N | N | Y | N |
| 07-10-005 | L | L | N | N | N | N |
| 07-10-012 | L | L | N | N | N | N |
| 07-10-017 | L | L | N | Y | N | N |
| 08-01-022 | L | L | N | N | N | N |
| 08-01-031 | L | H | N | N | N | N |
| 08-01-043 | L | L | N | Y | N | N |
| 08-01-046 | L | L | N | N | N | N |
| 08-01-050 | H | L | N | Y | N | N |
| 08-01-051 | H | L | N | N | N | N |
| 08-01-056 | H | H | N | Y | N | N |
| 08-01-059 | L | L | N | N | N | N |
| 08-01-060 | H | H | N | Y | Y | N |
| 08-01-061 | H | L | N | N | N | N |
| 08-01-064 | L | L | N | Y | N | N |
| 08-01-069 | H | L | N | N | N | N |
| 08-01-070 | H | L | N | N | N | N |
| 08-01-071 | H | L | N | N | N | N |
| 08-01-072 | L | L | N | Y | N | N |
| 08-01-073 | L | H | N | N | N | Y |
| 08-02-006 | L | L | N | N | N | N |
| 08-02-011 | L | L | N | Y | N | N |
| 08-02-016 | H | L | N | N | N | N |
| 08-02-017 | H | L | N | N | Y | N |
| 08-03-008 | L | H | N | N | N | N |

The patients included in the Vx001-201 study were classed into several sub-groups: L for patients having a normal level for the marker considered, in accordance with the standards of the laboratory that carried out the determination, and H for the patients having a level higher than the normal limit established by each laboratory; N=No; Y=Yes; ND=not determined.

1. Clinical Response to Vx-001 and LDH Level

Among the 190 patients included in the Vx-001-201 study, 127 patients had a normal serum level of LDH. In this population, vaccination with Vx-001 enabled the OS and the TTF to be significantly increased relative to the patients in the placebo group (FIG. 1).

2. Clinical Response to Vx-001 and gGT Level

Among the 190 patients included in the Vx-001-201 study, 139 patients had a normal serum level of gGT. In this population, vaccination with Vx-001 enabled the OS to be increased relative to the patients in the placebo group, but not significantly (p=0.10). In contrast, the TTF significantly increased (FIG. 2).

3. Clinical Response to Vx-001 and Alkaline Phosphatase (ALP)

Among the 190 patients included in the Vx-001-201 study, 160 patients had a normal serum level of ALP. In this population, vaccination with Vx-001 did not cause an increase in OS relative to the patients in the placebo group (p=0.74, FIG. 3). The patient's level of ALP did not impact the patients' capacity to respond to Vx-001. The results concerning the TTF are identical.

4. Clinical Response to Vx-001 and Blood Count

Blood count is commonly used to assess a patient's inflammatory state. Thus, in addition to the absolute number of neutrophils, the ratio between the number of neutrophils and of lymphocytes as well as the number of platelets are characteristic of the general state of a patient's health.

a. Clinical Response to Vx-001 and Absolute Number of Neutrophils

The absolute number of neutrophils is a commonly used marker of inflammation. It has been shown in particular that a high number of neutrophils was associated with a weak response to treatment with immune checkpoint inhibitors (ICI's) (Ferrucci et al., Annals Oncol 2016).

In the case of treatment with Vx-001, the number of neutrophils was not observed to have any impact. No difference in survival was observed between the patients of the placebo group and those having received the treatment, either in the patients having a high level of neutrophils, or in those in which it was normal (FIG. 4).

b. Clinical Response to Vx-001 and Ratio Between Neutrophils and Lymphocytes

The same type of result was observed with the ratio between the number of neutrophils and lymphocytes. No difference in survival was observed between the patients of the placebo group and those having received the treatment, either in the patients having a ratio between neutrophils and lymphocytes less than 3, a ratio commonly used as a limit in the literature (Mezquita et al., 2018; Ferrucci et al., 2016), or with those in which it was higher than 3 (FIG. 5).

c. Clinical Response to Vx-001 and Platelets

Lastly, the number of platelets has no impact. No difference in survival was observed between the patients of the placebo group and those having received the treatment, either in the patients having a high level of platelets, or in those in which it was normal (UNL: "Upper Normal Limit") (FIG. 6).

5. Combined Factors a. gGT and LDH

The clinical effectiveness of Vx-001 was next assessed when combining the factors, in particular those which had shown an impact on the survival and the TTF of the patients.

In the 97 patients having a level of LDH and of gGT both normal, the treatment with Vx-001 very significantly increased the survival and the TTF: p=0.003 et p=0.0019, respectively (FIG. 7).

A more detailed analysis of the survival for the sub-groups of this population of patients with normal serum levels of LDH and gGT, shows that Vx-001 has a very significant effect in patients suffering from cancer that is non-squamous (or NSQ, p=0.0038), in men (p=0.0024), smokers (p=0.0099), patients less than 65 years old (p=0.0019), patients entering the study with an objective response to chemotherapy (OR, p=0.036) or with stable disease (SD, p=0.034), with an ECOG of 0 (0.041) or an ECOG of 1 (p=0.039). By contrast, and surprisingly, Vx-001 does not significantly increase the survival of patients whose cancer has a squamous histology (SQ, p=0.39), in women (p=0.27) and in patients over 65 years old (p=0.08) (FIG. 8).

Similarly, an analysis of the TTF of the sub-groups of this population of patients with normal serum levels of LDH and gGT, confirms that Vx-001 has a very strong effect in patients suffering from non-squamous cancer (NSQ, p=0.0009), in men (p=0.0064), smokers (p=0.001), patients younger than 65 years old (p=0.0017), patients who entered the study with an objective response to chemotherapy (OR, p=0.021), with an ECOG of 0 (0.021), but also in patients over 65 years old (p=0.0017).

By contrast, Vx-001 does not significantly increase the TTF of patients whose cancer has a squamous histology (SQ, p=0.49), in women (p=0.25) and in patients who entered the study with stable disease further to chemotherapy (SD, p=0.074) or an ECOG of 1 (p=0.14) (FIG. 9).

The combination of the levels of LDH and of gGT is the only combination of factors whose effect is synergistic, the other combinations giving results at best identical to the analysis with the level of LDH alone (FIG. 10).

6. Effect of the LDH and gGT Markers as a Function of the Immunogenicity of the Tumor The immunogenicity of a tumor depends on several factors of which the most important are the presence of TILs (Tumor Infiltrating Lymphocytes) within the tumor and the expression of the PD-L1 molecule by the tumor cells. We analyzed the effect of Vx-001 as a function of these two parameters on 136 patients for whom biopsy slides were available to us. The 22C3 pharmDx kit was used for detecting the PD-L1.

The expression of the PD-L1 was analyzed according to the recommendations of the Agilent kit which enable quantification of the tumor cells that express PD-L1 (TPS: tumor proportional score). The groups were classified into three groups i) PD-L1 negative (<1% of cells marked; TPS<1%), ii) PD-L1 positive (1-49% of cells marked; TPS 1-49%) and iii) over-expressing PD-L1 (>50% of cells positives; TPS>50%) Tumor infiltration (Intratrumoral Site, IS and Stromal Site, SS) by TILs was qualified into i) absent (score 0), ii) very rare (score 1), iii) low (score 2), iv) average (score 3) and v) high (score 4).

The tumors were classified as PD-L1 negative if less than 1% of the tumor cells expressed PD-L1 (TPS; Tumor Proportional Score; <1%) and TILs negative if the TILs in the tumor core and tumor stroma were totally absent (score 0) or very rare (score 1). The individual results are presented in Table 2.

TABLE 2 the TIL and TPS scores of patients for whom these data were available

| Patient | Arm | TIL (IS) | TIL (SS) | TPS |
|---|---|---|---|---|
| 01-02-004 | V | 0 | 0 | <1% |
| 01-03-007 | V | 0 | 0 | >50% |
| 01-03-012 | P | 1 | 4 | <1% |
| 01-03-018 | V | 0 | 0 | <1% |
| 01-03-023 | P | 0 | 3 | 1-49% |
| 01-04-011 | V | 0 | 1 | <1% |
| 01-05-001 | P | 1 | 2 | <1% |
| 01-05-011 | V | 1 | 3 | <1% |
| 01-06-006 | P | 1 | 2 | <1% |

TABLE 2-continued the TIL and TPS scores of patients for whom these data were available

| Patient | Arm | TIL (IS) | TIL (SS) | TPS |
|---|---|---|---|---|
| 01-08-002 | V | 1 | 2 | 1-49% |
| 01-08-003 | V | 2 | 3 | 1-49% |
| 01-08-005 | V | 0 | 2 | <1% |
| 01-09-002 | V | 1 | 2 | 1-49% |
| 01-09-006 | P | 0 | 0 | >50% |
| 01-10-002 | V | 1 | 1 | <1% |
| 01-10-004 | P | 0 | 0 | <1% |
| 02-03-001 | P | 2 | 2 | 1-49% |
| 02-06-005 | P | 1 | 2 | <1% |
| 02-07-004 | V | 0 | 0 | <1% |
| 02-07-007 | V | 0 | 1 | <1% |
| 03-01-005 | V | 0 | 1 | <1% |
| 03-01-008 | P | 2 | 2 | <1% |
| 03-02-001 | P | 2 | 3 | <1% |
| 03-02-042 | V | 1 | 1 | <1% |
| 03-03-015 | P | 0 | 0 | <1% |
| 03-03-019 | P | 1 | 3 | <1% |
| 03-03-020 | V | 1 | 1 | <1% |
| 03-03-023 | V | 0 | 0 | <1% |
| 03-03-025 | P | 1 | 3 | <1% |
| 03-03-028 | V | 1 | 4 | <1% |
| 03-03-031 | P | 0 | 2 | 1-49% |
| 03-03-049 | P | 0 | 0 | <1% |
| 03-03-058 | P | 1 | 2 | <1% |
| 03-03-062 | P | 0 | 0 | <1% |
| 03-03-065 | V | 0 | 2 | <1% |
| 03-03-086 | V | 0 | 0 | <1% |
| 03-04-001 | V | 1 | 2 | <1% |
| 03-04-014 | P | 1 | 0 | <1% |
| 03-04-025 | P | 1 | 0 | <1% |
| 03-04-042 | P | 0 | 1 | <1% |
| 03-05-006 | P | 0 | 3 | 1-49% |
| 03-05-007 | V | 0 | 2 | <1% |
| 03-06-005 | P | 1 | 3 | 1-49% |
| 03-06-012 | V | 0 | 1 | <1% |
| 03-06-016 | P | 0 | 0 | <1% |
| 03-07-001 | V | 1 | 3 | 1-49% |
| 03-07-007 | V | 0 | 0 | <1% |
| 03-07-008 | P | 0 | 1 | <1% |
| 03-07-013 | P | 0 | 1 | <1% |
| 03-07-060 | P | 0 | 0 | <1% |
| 03-07-066 | V | 0 | 0 | <1% |
| 03-07-071 | P | 1 | 2 | <1% |
| 03-08-013 | P | 0 | 0 | <1% |
| 03-08-014 | P | 0 | 1 | <1% |
| 03-10-001 | V | 2 | 4 | <1% |
| 04-01-023 | P | 1 | 4 | 1-49% |
| 04-01-057 | V | 0 | 0 | <1% |
| 04-02-002 | V | 1 | 3 | <1% |
| 04-03-008 | P | 1 | 3 | <1% |
| 04-03-010 | V | 1 | 2 | <1% |
| 04-04-002 | P | 0 | 2 | <1% |
| 04-05-002 | P | 1 | 2 | 1-49% |
| 04-05-026 | V | 1 | 3 | <1% |
| 04-05-036 | V | 0 | 0 | <1% |
| 04-06-001 | V | 1 | 3 | <1% |
| 04-06-002 | P | 0 | 0 | <1% |
| 04-07-013 | P | 1 | 3 | <1% |
| 04-07-021 | P | 1 | 2 | <1% |
| 04-07-029 | P | 1 | 4 | <1% |
| 04-09-005 | P | 1 | 4 | <1% |
| 04-10-007 | P | 1 | 2 | <1% |
| 04-10-008 | V | 1 | 3 | <1% |
| 04-10-014 | V | 1 | 2 | <1% |
| 04-10-024 | V | 1 | 4 | <1% |
| 04-10-031 | P | 0 | 0 | <1% |
| 04-10-034 | P | 0 | 1 | <1% |
| 04-12-001 | P | 1 | 2 | <1% |
| 04-12-002 | V | 0 | 0 | <1% |
| 04-12-009 | P | 0 | 1 | <1% |
| 04-13-003 | P | 0 | 0 | <1% |
| 04-13-004 | V | 0 | 0 | <1% |
| 04-13-011 | P | 1 | 3 | <1% |
| 04-13-015 | P | 1 | 3 | 1-49% |
| 05-01-013 | V | 1 | 1 | <1% |
| 05-03-003 | V | 0 | 0 | <1% |
| 05-04-012 | V | 0 | 0 | <1% |
| 05-06-005 | V | 2 | 4 | <1% |
| 05-07-006 | P | 2 | 4 | 1-49% |
| 05-09-004 | V | 1 | 1 | <1% |
| 05-09-006 | P | 0 | 0 | <1% |
| 05-09-008 | V | 1 | 3 | <1% |
| 05-11-001 | V | 1 | 3 | <1% |
| 05-11-007 | P | 1 | 4 | <1% |
| 07-02-004 | P | 0 | 0 | <1% |
| 07-03-002 | V | 1 | 2 | <1% |
| 07-03-004 | P | 0 | 1 | <1% |
| 07-03-011 | P | 2 | 3 | >50% |
| 07-03-015 | V | 1 | 2 | 1-49% |
| 07-03-016 | P | 1 | 2 | <1% |
| 07-03-019 | V | 1 | 2 | <1% |
| 07-03-021 | P | 1 | 3 | >50% |
| 07-03-022 | V | 1 | 2 | 1-49% |
| 07-03-030 | V | 0 | 1 | <1% |
| 07-03-032 | V | 0 | 0 | <1% |
| 07-04-006 | V | 1 | 3 | <1% |
| 07-04-010 | P | 1 | 2 | <1% |
| 07-04-011 | P | 0 | 1 | >50% |
| 07-04-020 | V | 1 | 3 | 1-49% |
| 07-04-023 | P | 0 | 0 | 1-49% |
| 07-05-001 | V | 1 | 3 | <1% |
| 07-06-006 | V | 1 | 3 | <1% |
| 07-06-016 | V | 0 | 0 | <1% |
| 07-06-018 | V | 1 | 3 | 1-49% |
| 07-06-020 | V | 1 | 1 | <1% |
| 07-07-011 | V | 0 | 0 | <1% |
| 07-08-001 | P | 0 | 0 | <1% |
| 07-10-002 | P | 1 | 2 | 1-49% |
| 07-10-005 | V | 0 | 0 | <1% |
| 07-10-012 | V | 0 | 0 | <1% |
| 07-10-017 | P | 1 | 2 | 1-49% |
| 08-01-043 | P | 0 | 0 | <1% |
| 08-01-046 | P | 0 | 0 | <1% |
| 08-01-050 | V | 0 | 1 | 1-49% |
| 08-01-051 | P | 0 | 0 | <1% |
| 08-01-056 | V | 1 | 3 | <1% |
| 08-01-059 | V | 1 | 3 | <1% |
| 08-01-060 | V | 1 | 2 | <1% |
| 08-01-061 | V | 1 | 2 | >50% |
| 08-01-064 | P | 0 | 1 | <1% |
| 08-01-069 | P | 1 | 3 | <1% |
| 08-01-070 | V | 0 | 1 | <1% |
| 08-01-071 | P | 1 | 2 | >50% |
| 08-01-072 | P | 1 | 3 | <1% |
| 08-01-073 | P | 0 | 1 | >50% |
| 08-02-016 | P | 1 | 2 | <1% |
| 08-03-008 | P | 0 | 1 | >50% |

The results presented in FIG. 11 show that Vx-001 extends the survival of patients who have tumors that are negative for TIL (8.7 vs 20.7 months, p=0.0089) and for PD-L1 (9.9 vs 15.5 months; p=0.13) but does not extend the survival of patients who have tumors that are positive for TIL (16.3 vs 14.3 months; p=0.197) and for PD-L1 (24.9 vs 7.9 months; p=0.29). The clinical effectiveness of Vx-001 is still greater in patients with tumors which are both TIL- and PD-L1-(6.6 vs 20.7 months p=0.0049). Similar results were obtained with the analysis of the TTF. The Vx-001 extended the TTF in patients who had TIL-tumors (2.7 vs 3.6 months; p=0.041). PD-L1-(2.3 vs 3.5 months; p=0.079) and TIL-/PD-L1-(2.2 vs 3.6 months; p=0.011) (FIG. 12).

The analysis of the effect of both the factors LDH and gGT according to the immunogenicity of the tumors, defined by the presence of TILs and the expression of PD-L1, showed that the normal level of serum LDH and of serum gGT correlated with a longer survival (FIG. 13) and a longer TTF (FIG. 14) in patients who have non-immunogenic tumors (TIL-, PD-L1-, TIL-/PD-L1-) but not in patients who have immunogenic tumors (TIL+, PD-L1+, TIL+ and/or PDI-L1+).

REFERENCES

Ferrucci P F, Ascierto P A, et al., *Baseline neutrophils and derived neutrophil-to-lymphocyte ratio: prognostic relevance in metastatic melanoma patients receiving ipilimumab*. Ann Oncol. 2016 April; 27(4):732-8.

Georgoulias V, et al., *A multicenter randomized phase IIb efficacy study of Vx-*001*, a peptide-based cancer vaccine as maintenance treatment in advanced non-small-cell lung cancer: treatment rationale and protocol dynamics*. Clin Lung Cancer. 2013 July; 14(4):461-5.

Menez-Jamet J, et al., *Optimized tumor cryptic peptides: the basis for universal neo-antigen-like tumor vaccines*. Ann Transl Med. 2016 July; 4(14):266.

Mezquita, L. et al., Association of the Lung Immune Prognostic Index With Immune checkpoint Inhibitor Outcomes in Patients With Advanced Non-Small Cell Lung Cancer. JAMA Oncol. 2018 Mar. 1; 4(3):351-357. Tourdot S, et al., *A general strategy to enhance immunogenicity of low-affinity HLA-A*2*. 1-associated peptides: implication in the identification of cryptic tumor epitopes*. Eur J Immunol. 2000 December; 30(12):3411-21.

The invention claimed is:

1. A method of prolonging survival and/or time to failure (TFF) of a HLA-A*0201-positive patient having a lung tumor expressing Telomerase Reverse Transcriptase (TERT) comprising a step of selecting a HLA-A*0201-positive patient having a lung tumor expressing Telomerase Reverse Transcriptase (TERT) and who has a normal level of gamma Glutamine Transferase (gGT) and/or a normal level of lactate dehydrogenase (LDH) and a step of administering a Vx-001 anti-cancer vaccine comprising a peptide of SEQ ID NO: 2 and a peptide of SEQ ID NO: 1 to the selected patient, wherein the administering of the Vx-001 anti-cancer vaccine to the selected patient prolongs survival and/or TFF of the patient as compared to placebo.

2. The method of claim 1, wherein the patient has a normal level of gGT and a normal level of LDH.

3. The method of claim 1, wherein the patient suffers from a non-small cell lung cancer.

4. The method of claim 1, wherein the Vx-001 anti-cancer vaccine is administered to the patient further to a first-line chemotherapy.

5. The method of claim 1, wherein the patient is a male patient.

6. The method of claim 1, wherein the patient has a non-squamous tumor.

7. The method of claim 1, wherein the patient is less than 65 years old.

8. The method of claim 1, wherein the patient has cancer which is no longer progressing after a first-line chemotherapy.

9. The method of claim 1, wherein the patient has an Eastern Cooperative Oncology Group functional index (ECOG) score of 0.

```
                         SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: peptide from a human protein

<400> SEQUENCE: 1

Arg Leu Phe Phe Tyr Arg Lys Ser Val
1               5


<210> SEQ ID NO 2
<211> LENGTH: 9
<212> TYPE: PRT
<213> ORGANISM: Artificial Sequence
<220> FEATURE:
<223> OTHER INFORMATION: optimized peptide

<400> SEQUENCE: 2

Tyr Leu Phe Phe Tyr Arg Lys Ser Val
1               5
```

10. The method of claim 1, wherein the patient has a tumor which does not express the PD-L1 molecule and/or is not infiltrated with lymphocytes.

* * * * *